United States Patent [19]

Sarnoff et al.

[11] 4,329,988

[45] May 18, 1982

[54] PLURAL INJECTION ASSEMBLY

[75] Inventors: Stanley J. Sarnoff; Claudio Lopez, both of Bethesda, Md.

[73] Assignee: Survival Technology, Inc., Bethesda, Md.

[21] Appl. No.: 219,488

[22] Filed: Dec. 23, 1980

[51] Int. Cl.³ .............................................. A61M 5/00
[52] U.S. Cl. ................................................ 128/218 F
[58] Field of Search ................... 128/215, 216, 218 R, 128/218 F, 218 D, 218 DA, 218 A, 234

[56] References Cited

U.S. PATENT DOCUMENTS

| | | | |
|---|---|---|---|
| 2,832,339 | 4/1958 | Sarnoff | 128/218 |
| 3,702,609 | 11/1972 | Steiner | 128/218 |
| 3,881,863 | 5/1975 | Sarnoff | 128/218 |
| 4,226,235 | 10/1980 | Sarnoff | 128/218 |

*Primary Examiner*—John D. Yasko
*Attorney, Agent, or Firm*—Cushman, Darby & Cushman

[57] ABSTRACT

A plural injection assembly comprising a plurality of separate injections capable of separate actuation and a holder for stably supporting the separate injectors together and for manually facilitating the sequential actuation thereof.

6 Claims, 8 Drawing Figures

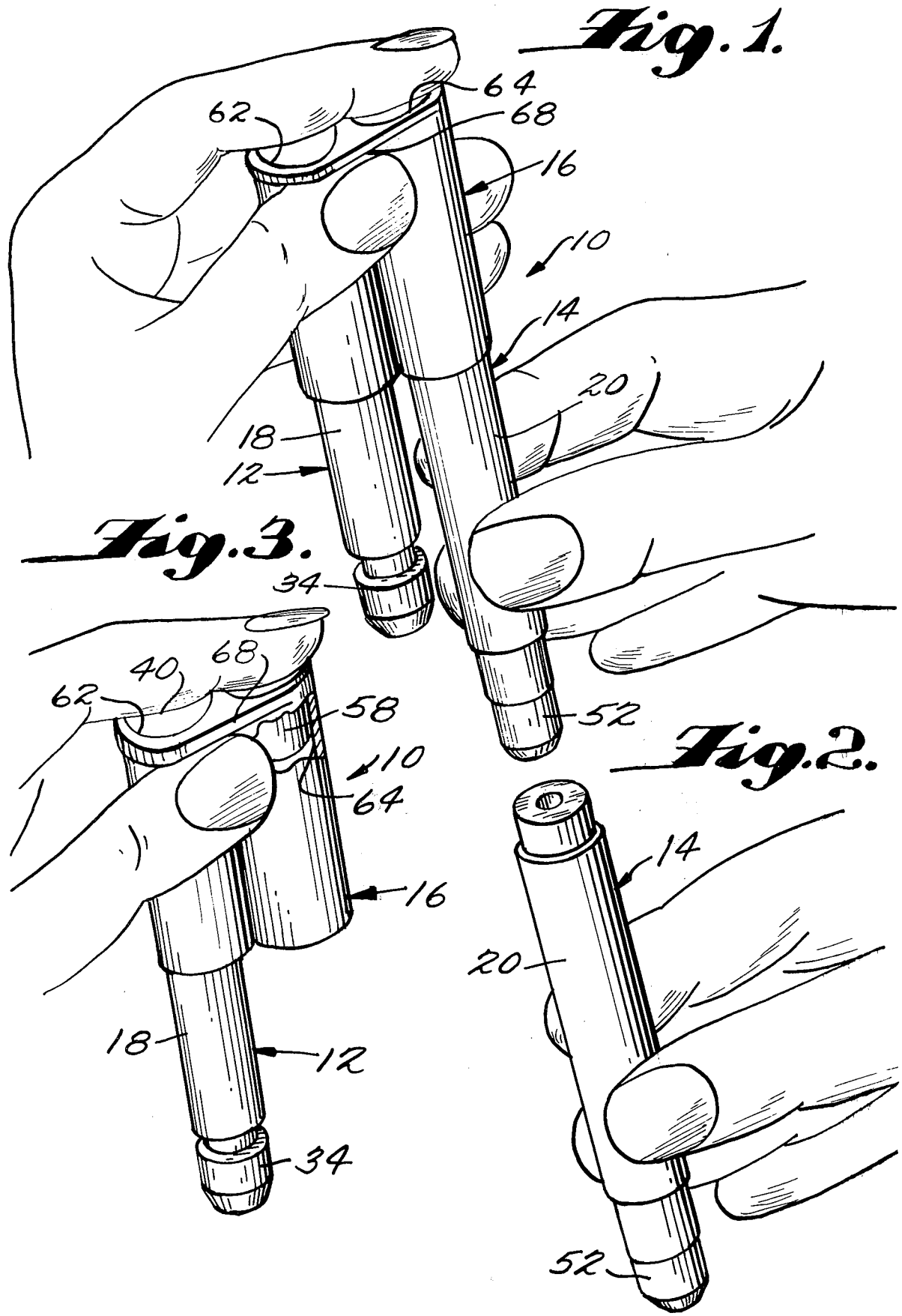

PLURAL INJECTION ASSEMBLY

BACKGROUND AND SUMMARY OF THE INVENTION

This invention relates to injecting devices and more particularly to improvements in injection assemblies capable of a plurality of separate injections.

Injectors of the so-called "automatic" type are well known. Examples of injectors of this type are contained in Sarnoff et al. U.S. Pat. No. 2,832,339 and Sarnoff et al. U.S. Pat. No. 3,882,863. Injectors having the construction embodied in these two patents have been constructed so as to contain a chemical warfare antidote dosage for use by military personnel. Another example of an injector of the automatic type is disclosed in U.S. Pat. No. 3,702,609. The injectors disclosed in all of these patents are single dosage injectors.

In many situations now presented it has become necessary to provide military personnel with the capability of self-injecting a plurality of separate medicament dosages as, for example, 2 mg of atropine and 600 mg of pralidoxime chloride. Current practice is to provide two separate injectors which military personnel must handle separately and actuate separately. Under the circumstances where the injection of such plural dosages is needed it is important that personnel accomplish the injection procedure as rapidly as possible. The provision of separate injectors does not serve to facilitate the accomplishment of the actuation of both injectors. For example, the handling of more than one injector at a time is difficult because the actuation of each injector requires both hands. Moreover, by having each injector separate there exists the possibility that they are not conveniently together when use is required.

In Sarnoff et al. U.S. Pat. No. 4,226,235 there is disclosed a plural injection assembly which not only serves to unitize two separate injectors but to unitize them in such a way that a single actuation will insure the simultaneous or substantially simultaneous actuation of all of the injectors. For example, in FIG. 7 of the aforesaid patent, there is disclosed an arrangement by which a small dosage injector constructed in accordance with Sarnoff et al. U.S. Pat. No. 2,832,339 and a relatively large dosage injector constructed in accordance with Sarnoff et al. U.S. Pat. No. 3,882,863 are unitized in an arrangement capable of a simultaneous injection in response to a single actuation.

The present invention has for its object the provision of a plural injection assembly which embodies a plurality of separate injectors capable of separate actuation such as those presently provided and a holder for stably supporting the separate injectors together and for manually facilitating the sequential actuation thereof. The holder consists essentially of a one-piece molded plastic body which is easily disposed in supported relation with respect to the plurality of separate injectors such that the assembly can be either accomplished manually by furnishing the holder to military personnel already provided with separate injectors or by providing simple preassembly either manually or by machine. In the assembly constructed in accordance with the principles of the present invention, each injector includes the usual exterior housing having a needle, a medicament dosage and a stressed spring assembly mounted therein in cooperating relation such that upon actuation of the injector the associated stressed spring assembly is released to move the associated needle into the muscle tissue of a user and the associated medicament dosage outwardly through the needle into the muscle tissue. Each injector also includes an arming member preferably in the form of an arming pin on an end cap mounted for movement from (1) a normal position exposed exteriorly with respect to the associated housing and operatively connected with the associated stressed spring assembly for preventing actuation of the injector and release of the associated spring assembly for enabling the latter to be released upon actuation of the associated injector. The holder is mounted in retaining engagement with each arming member and in removable supporting relation over an adjacent portion of each housing so as to stably support the injectors together with a substantial portion of their housings exposed in a convenient position to be sequentially grasped by one hand of a user when the holder is grasped by the other hand, thereby enabling the user to manually remove from the holder each injector in an armed condition ready for actuation and release of the stressed spring assembly thereof by virtue of the retention of the associated arming member in engagement with the holder.

Another object of the present invention is the provision of a plural injection assembly of the type described which is simple in construction, effective in operation and economical to manufacture.

These and other objects of the present invention will become more apparent during the course of the following detailed description and appended claims.

The invention may best be understood with reference to the accompanying drawings, wherein an illustrative embodiment is shown.

DETAILED DESCRIPTION OF THE DRAWINGS

FIG. 1 is a perspective view of a plural injection assembly embodying the principles of the present invention illustrating the manner in which the assembly is initially manually grasped by both hands of the user;

FIG. 2 illustrates the removal of the initial injector grasped by one hand in FIG. 1 illustrating the injector still in the grasp of the same hand of the user;

FIG. 3 is a perspective view with parts broken away of the remaining components of the assembly, illustrating the same in the grasp of the other hand of the user after the initial injector shown in FIG. 2 has been removed from the assembly;

DETAILED DESCRIPTION OF THE INVENTION

Figure 4:
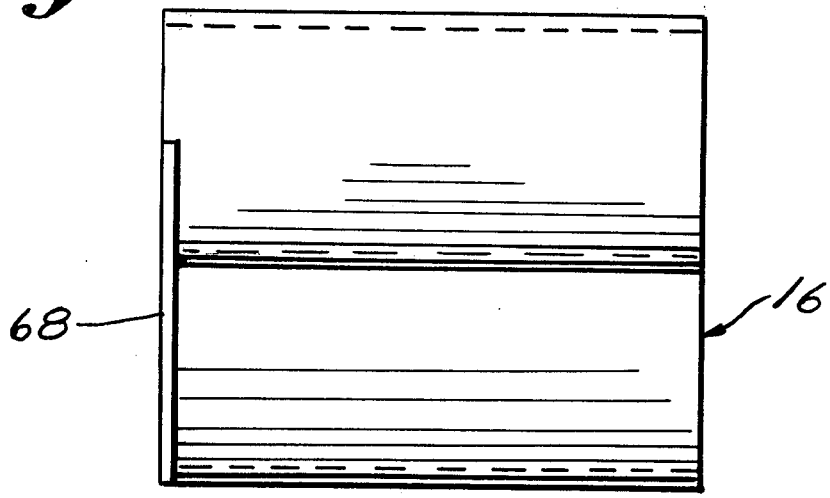
FIG. 4 is a top plan view of the holder of the present assembly.
Figure 5:
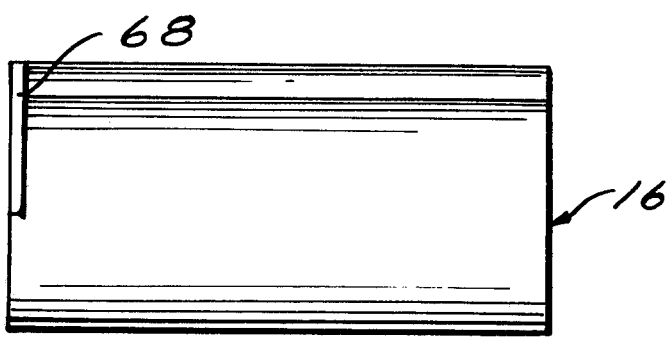
FIG. 5 is a side elevational view of the holder.
Figure 6:
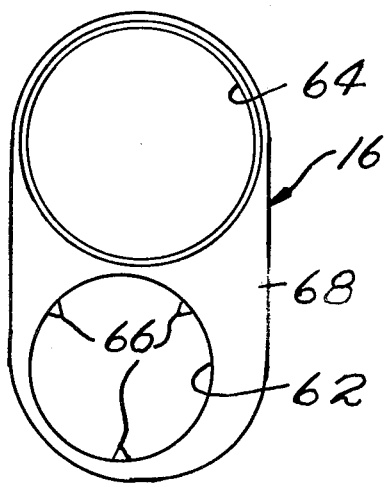
FIG. 6 is a left-hand end view of the holder.
Figure 7:
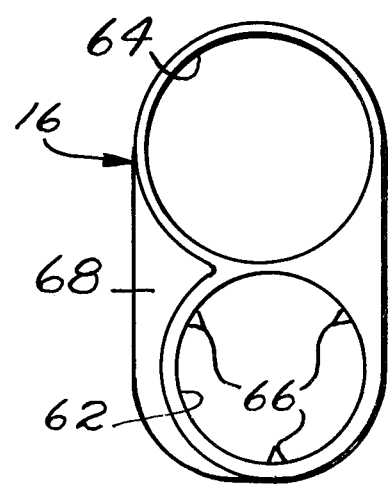
FIG. 7 is a right-hand end view of the holder.

Referring now more particularly to the drawings, there is shown in FIG. 1 thereof a plural injection assembly, generally indicated at 10, which embodies the principles of the present invention. In the preferred embodiment shown, the assembly 10 consists essentially of three basic components; namely, two separate injectors, generally indicated at 12 and 14 respectively, and a holder, generally indicated at 16. It will be understood that more than two injectors may be utilized in the assembly. The injectors utilized are of the so-called "automatic" type and any of the well known constructions of this type of injector may be used. In the preferred embodiment shown in the drawings the injector 12 is constructed in accordance with the teachings contained in Sarnoff et al. U.S. Pat. No. 2,832,339 and the injector 14 is constructed in accordance with the teachings contained in Sarnoff et al. U.S. Pat. No. 3,882,863. Accordingly, the disclosures of both of these patents are hereby incorporated by reference into the present specification.

It will be understood that a common characteristic of all automatic injectors including the injector of U.S. Pat. No. 3,702,609 as well as the two noted above is that they have a housing within which there is mounted a hypodermic needle, a medicament dosage and a stressed spring assembly. The injector is capable of being actuated by the user but only after the user has armed the injector by removing an arming member. Upon actuation, the stressed spring assembly is released to effect movement of the needle outwardly into the muscle tissue of the user and the medicament outwardly through the needle into the muscle tissue.

Figure 8:
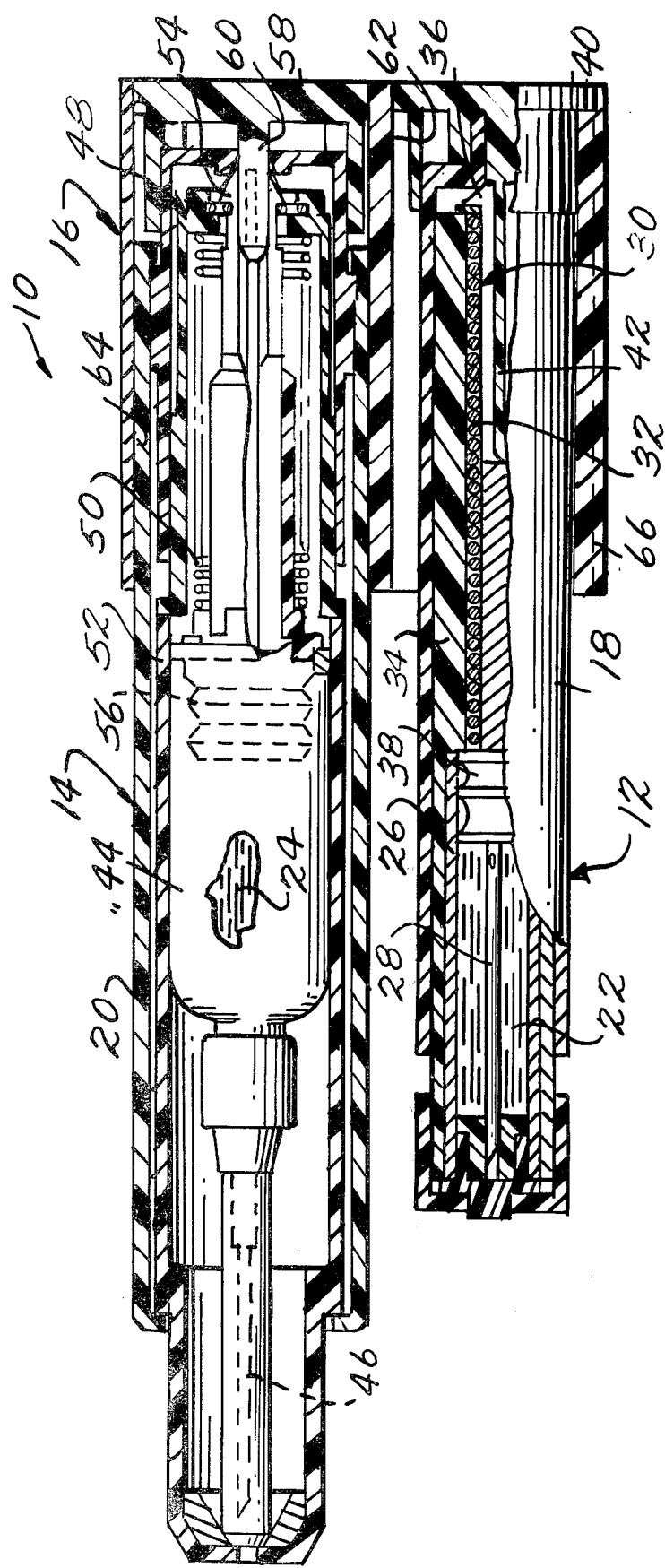
FIG. 8 is an enlarged cross-sectional view of the assembly.

Referring now more particularly to FIG. 8 wherein the injectors 12 and 14 are shown in cross-section, it will be noted that injector 12 includes a housing 18 which is relatively short with respect to a relatively long housing 20 embodied in the injector 14. The relatively short housing 18 includes therein a relatively small medicament dosage 22, while the longer and larger housing 20 includes therein a relatively large medicament dosage 24.

Because of its relatively small size, dosage 22 is contained within a stationary container 26 within housing 18 having a hypodermic needle 28 mounted therein for outward longitudinal movement with respect thereto. Outward movement of the needle 28 is accomplished by a stressed spring assembly, generally indicated at 30. Spring assembly 30 includes coil spring 32 stressed between an interior structure 34 releasably holding spring fingers 36 and a plunger 38. Spring fingers 36 are retained against release by an arming member 40 which, as shown, is in the form of a skirted cap having a peripheral size greater than that of the cylindrical housing 18 and a depending arming pin 42.

When arming member 40 is disposed on the end of the housing 18, arming pin 42 extends within the releasable fingers 36 preventing their radially inwardly movement into a releasing position. Removal of the arming cap 38 disposes the injector 12 in an armed condition so that when the housing 18 is manually grasped and the end of the interior structure 34 projecting from the opposite end of the housing 18 is engaged with the thigh of the user a relative movement between the interior structure 34 and housing 18 causes spring fingers 36 to be moved inwardly into their releasing position whereupon, stressed spring 32 acts to move plunger outwardly which carries with it needle 28 and dosage 22. Needle 28 thus moves outwardly and into the user's muscle tissue while dosage 22 is moved outwardly through the needle.

The relatively larger dosage 24 of the injector 14 is contained within a movable container 44 having a hypodermic needle 46 fixed to the leading end thereof. A stressed spring assembly 48 is provided which includes coil spring 50 stressed between an interior structure 52 releasably holding spring fingers 54 and a plunger 56. As before, spring fingers 54 are retained against release by an arming member 58 also in the form of a relatively large size skirted cap having a depending arming pin 60. The arming member 58 operates, as before, to normally prevent actuation and when removed to permit actuation. Actuation is similar except that the dosage container 44 is moved outwardly with the needle 46.

The holder 16 is preferably molded as a one-piece body of suitable plastic material, as, for example, polypropylene. The holder body is configured so as to stably support the two separate injectors together and to facilitate the manual sequential activation thereof. To this end, the holder body is formed in a pair of parallel openings 62 and 64 which extend completely therethrough. The opening 62 has its interior periphery configured to receive the injector 12 for longitudinal movement therein, needle end first, into the position shown in FIGS. 1 and 8 wherein arming cap member 40 is disposed in retained relation against further longitudinal movement in the needle end first direction and housing 18 is disposed in supported relation for removed longitudinal movement in the aforesaid needle end first direction. As shown, these functional relationships are accomplished by providing three or more longitudinally extending ribs 66 on the interior periphery of the opening 62. In a similar fashion, the interior periphery of the opening 64 is configured to receive the injector 14 for longitudinal movement therein, needle end first, into the position shown in FIGS. 1 and 8 wherein arming cap member 40 is disposed in retained relation against further longitudinal movement in the needle end first direction and housing 20 is disposed in supported relation for removed longitudinal movement in the aforesaid needle end first direction. These functions are achieved by providing the opening with a smooth interior periphery which tapers slightly.

It is important to note that the holder body extends over a portion of each injector housing adjacent to the arming members when in the assembled position shown in FIGS. 1 and 8 so that the remaining portion of each housing is exposed to be conveniently manually grasped by one hand of the user so as to accomplish the aforesaid removed movement thereof. It is also important to note that the exterior periphery of the holder body is configured to facilitate its being grasped and held in the other hand of the user. To this end, there is provided a flange 68 which extends outwardly along one side of the holder body at the cap end thereof. As best shown in FIG. 1, this flange 68 is thus positioned to engage the fingers of the user's hand when the user is pulling on the housing of an injector with the other to accomplish the removal thereof from supported relation with the holder.

It can be seen that in the assembled position of the plural injection assembly 10, holder 16 serves to stably support the two injectors 12 and 14 together so that both will be available when needed. The assembly 10 facilitates actuation of the separately held injectors 12 and 14 in the following manner. When it becomes necessary to use the assembly 10, the user grasps the holder 16 in one hand as shown in FIG. 1 so that the exposed portions of the housings 18 and 20 extend downwardly. The user is then able to quickly and conveniently grasp the exposed portion of one of the housings, as, for example, housing 20 as shown in FIGS. 1 and 2 with the other hand. With the hands in the position shown in FIG. 1 it is a simple matter for the user to pull downwardly on the housing 20 until it is removed from supported relation with the holder 16, as shown in FIG. 2.

It is important to note that the associated arming member 40 is retained within the holder so that the injector 14 in the removed position of FIG. 2 is in an armed condition ready to be actuated. Thus by simply continuing the manual movement of the housing 20 into engagement with the user's thigh, actuation can be readily accomplished. Actuation results in the release of the stressed spring assembly 30 which in turn moves needle 28 outwardly into the muscle tissue and dosage 22 outwardly through the needle 28 into the muscle tissue of the thigh.

While the injector 14 is thus being actuated to inject dosage 22, the holder 16 is retained in the user's grasped hand with housing 18 of injector 12 exposed in a convenient position to be gripped, as shown in FIG. 3. After the first injector 14 has been withdrawn and discarded, the exposed portion of housing 18 of the injector 12 is then grasped in the other hand and pulled as before. Also, as before, the movement of the housing 18 into its removed position in relation to holder results in the retention of arming member 58 with the holder 16 thus instantaneously placing the injector 12 in an armed condition for immediate actuation which can be readily accomplished as aforesaid.

It will be noted that the arrangement is such that existing separate injectors can be assembled within a cooperating holder either manually by the user or by mass production methods either manually or machine.

It thus it will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A plural injection assembly comprising
a plurality of separate injectors capable of separate actuation, each injector comprising an exterior housing having a needle, a medicament dosage and a stressed spring assembly mounted therein in cooperating relation such that upon actuation of the injector the associated stressed spring assembly is released to move the associated needle into the muscle tissue of a user and the associated medicament dosage outwardly through the needle into the muscle tissue and an arming member mounted for movement from (1) a normal position exposed exteriorly with respect to the associated housing and operatively connected with the associated stressed spring assembly for preventing actuation of said injector and release of the associated stressed spring assembly and into (2) a separated position with respect to both the associated housing and the associated stressed spring assembly for enabling the latter to be released upon actuation of the associated injector, and
a holder mounted in retaining engagement with each arming member and in removable supporting relation over an adjacent portion of each housing so as to stably support said injectors together with a substantial portion of their housings exposed in a convenient position to be sequentially grasped by one hand of a user when said holder is grasped by the other hand thereby enabling the user to manually remove from said holder each injector in an armed condition ready for actuation and release of the stressed spring assembly thereof by virtue of the retention of the associated arming member in engagement with said holder.

2. A plural injection assembly as defined in claim 1 wherein said holder comprises a unitary body molded of plastic material.

3. A plural injection assembly as defined in claim 2 wherein each housing is generally cylindrical and each arming member comprises a cap at one end of the associated cylindrical housing having a peripheral size greater than the peripheral size of the associated housing, said holder body having an opening extending completely therethrough having interior peripheral surface means operable to mount an associated injector in retaining engagement with the arming member thereof and in removable supporting relation over the adjacent portion of the housing thereof in response to a relative movement between the holder and associated injector into said opening in the same direction as the direction in which the injector is removed from the holder.

4. A plural injector assembly as defined in claim 3 wherein said holder body includes a flange at an end thereof opposed to the end from which the injectors are removed.

5. A plural injection assembly as defined in claim 1, 2, 3 or 4 wherein said plurality of injectors includes one in which the medicament dosage is relatively small and the housing is relatively short and one in which the medicament dosage is relatively large and the housing is relatively long.

6. A plural injection assembly comprising
a plurality of separate injectors capable of separate actuation and a holder for stably supporting said separate injectors together and for manually facilitating the sequential actuation thereof,
each of said injectors including an exterior housing having a needle, a medicament dosage and a stressed spring assembly mounted therein in cooperating relation such that upon actuation of the injector the associated stressed spring assembly is released to move the associated needle into the muscle tissue of a user and the associated medicament dosage outwardly through the needle into the muscle tissue,
said holder having disposed in a retained relation therewith an arming member for each of said injectors mounted for movement with respect to the associated injector from (1) a normal position operatively connected with the associated stressed spring assembly for preventing actuation of the associated injector and release of the associated stressed spring assembly thereof and into (2) a separated position with respect to both the associated housing and the associated stressed spring assembly for enabling the latter to be released upon actuation of the associated injector,
said holder being mounted in removable supporting relation over a portion of each housing so as to stably support said injectors together with a substantial portion of their housings exposed in a convenient position to be sequentially grasped by one hand of a user when said holder is grasped by the other hand thereby enabling the user to manually remove from said holder each injector in an armed condition ready for actuation and release of the stressed spring assembly thereof by virtue of the retention of the associated arming member with said holder.

* * * * *